(12) United States Patent
Kim et al.

(10) Patent No.: US 10,391,110 B2
(45) Date of Patent: Aug. 27, 2019

(54) COMPOSITION FOR PREVENTING OR TREATING VASCULAR LEAK SYNDROME

(71) Applicant: INTELLIGENT SYNTHETIC BIOLOGY CENTER, Daejeon (KR)

(72) Inventors: Ho Min Kim, Daejeon (KR); Ji In Kang, Seoul (KR); Sun Chang Kim, Daejeon (KR); Chang Hao Cui, Daejeon (KR)

(73) Assignee: Intelligent Synthetic Biology Center, Daejeon (KR)

( * ) Notice: Subject to any disclaimer, the term of this patent is extended or adjusted under 35 U.S.C. 154(b) by 0 days.

(21) Appl. No.: 15/511,586

(22) PCT Filed: May 19, 2016

(86) PCT No.: PCT/KR2016/005318
§ 371 (c)(1),
(2) Date: Mar. 15, 2017

(87) PCT Pub. No.: WO2017/010673
PCT Pub. Date: Jan. 19, 2017

(65) Prior Publication Data
US 2018/0289727 A1    Oct. 11, 2018

(30) Foreign Application Priority Data

Jul. 16, 2015 (KR) .................. 10-2015-0101239

(51) Int. Cl.
*A61P 7/00* (2006.01)
*A61P 7/10* (2006.01)
*A61K 31/704* (2006.01)

(52) U.S. Cl.
CPC ............ *A61K 31/704* (2013.01); *A61P 7/00* (2018.01); *A61P 7/10* (2018.01)

(58) Field of Classification Search
CPC ............. A61K 31/704; A61P 7/00; A61P 7/10
See application file for complete search history.

(56) References Cited

U.S. PATENT DOCUMENTS

2003/0190378 A1* 10/2003 Kim .................... A61K 31/366
424/728

FOREIGN PATENT DOCUMENTS

| EP | 2495242 A2 | 9/2012 | |
|---|---|---|---|
| JP | 2002-322068 | 11/2002 | |
| JP | 2005-298510 | 10/2005 | |
| KR | 10-2008-0034154 | 4/2008 | |
| KR | 10-958578 | 1/2010 | |
| KR | 10-2011-0047170 | 5/2011 | |
| KR | 10-1239495 | 7/2012 | |
| WO | WO-2006001654 A1 * | 1/2006 | ........... A61K 36/258 |
| WO | WO 2010/081172 | 7/2010 | |
| WO | WO 2014/025127 | 2/2014 | |
| WO | WO 2006/001654 | 1/2016 | |

OTHER PUBLICATIONS

Definition of prevent, Oxford English Dictionary Online, http://dictionary.oed.com/, accessed online Mar. 27, 2010, especially definition 9a. at p. 2. (Year: 2010).*
Baluna et al., Immunopharmacol., 1997, 37, p. 117-132. (Year: 1997).*
Entry for Systemic capillary leak syndrome, Mayo Clinic, https://www.mayoclinic.org/diseases-conditions/systemic-capillary-leak-syndrome, accessed online on Dec. 18, 2018. (Year: 2018).*
He et al. "Effects of component of some Chinese herbs on proliferation of human umbilical vein endothelial cells in vitro." *Chinese Journal of Pathophysiology* 5 (2004): 029. (English Abstract).
Maeng et al. "Rk1, a ginsenoside, is a new blocker of vascular leakage acting through actin structure remodeling." *PloS one* 8.7 (2013): e68659.
Yao et al. "Chemical fingerprinting and quantitative analysis of a Panax notoginseng preparation using HPLC-UV and HPLC-MS." *Chinese medicine* 6.1 (2011): 9.
Office Communication issued in Indian Patent Application No. 201717008861, dated Oct. 31, 2018.

* cited by examiner

*Primary Examiner* — Jonathan S Lau
(74) *Attorney, Agent, or Firm* — Parker Highlander PLLC

(57) ABSTRACT

The present invention relates to a pharmaceutical composition containing ginsenoside F1 or Rh1 for preventing or treating vascular leak syndrome, to a method for treating vascular leak syndrome using the pharmaceutical composition, and to a food composition containing ginsenoside F1 or Rh1 for preventing or ameliorating vascular leak syndrome. The ginsenoside F1 or Rh1 provided in the present invention can promote angiogenesis and suppress vascular leakage, and thus can be widely utilized in the effective prevention or treatment of vascular leak syndrome.

2 Claims, 13 Drawing Sheets

[FIG. 1A]
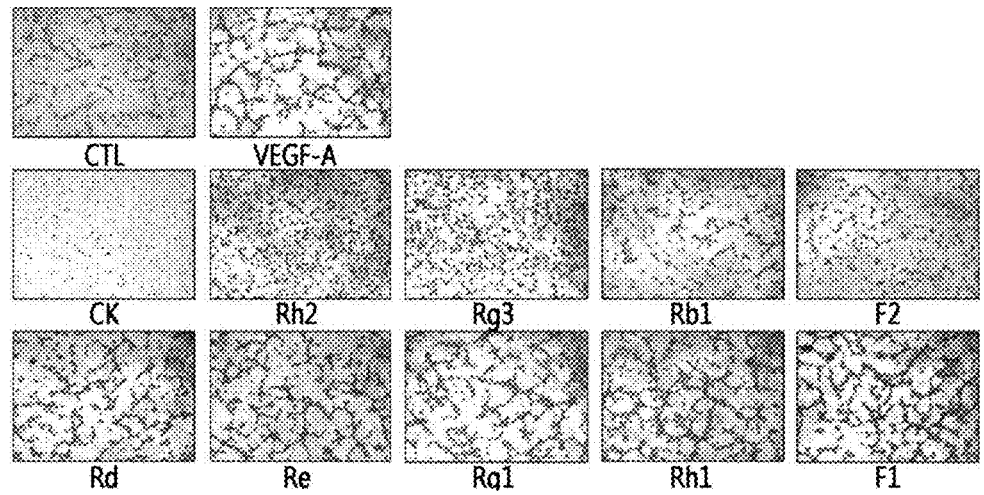
[FIG. 1B]
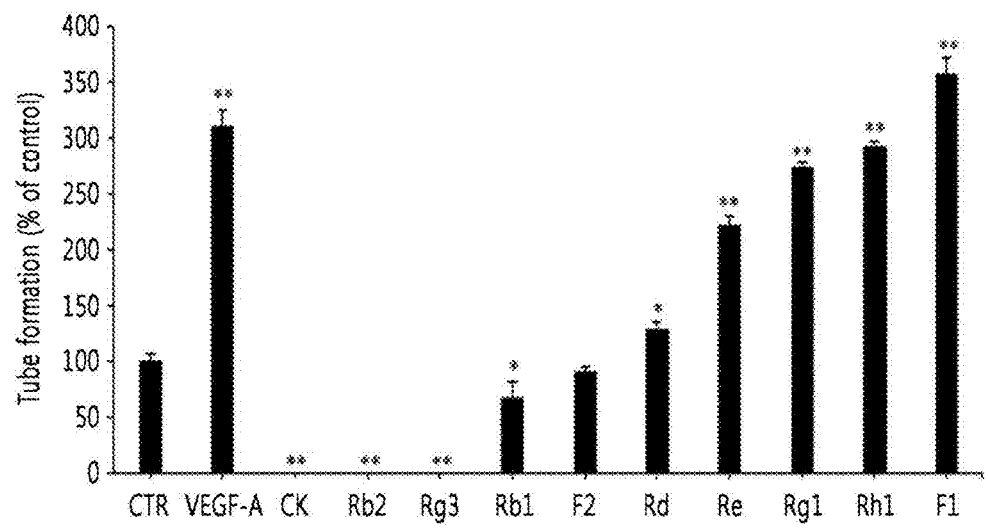

[FIG. 2A]
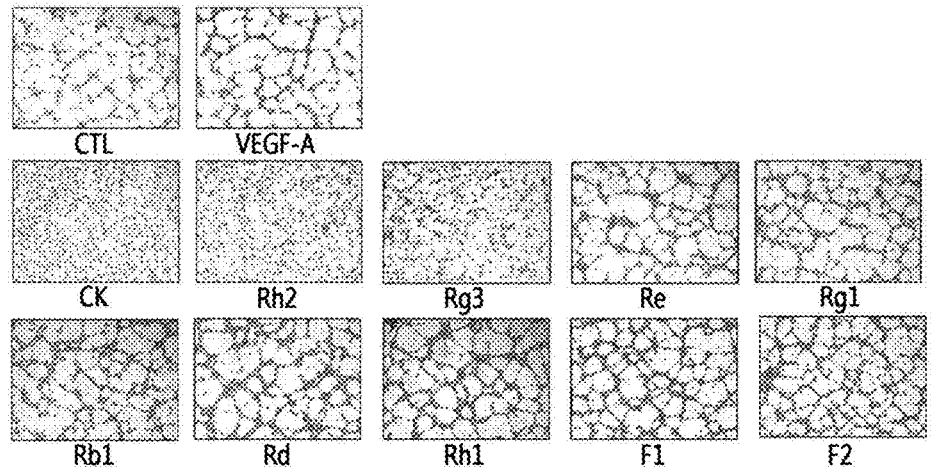
[FIG. 2B]
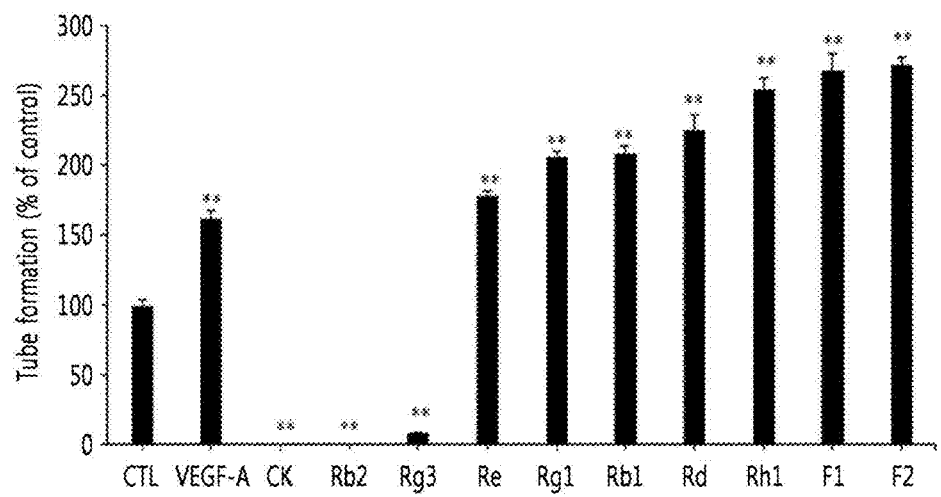

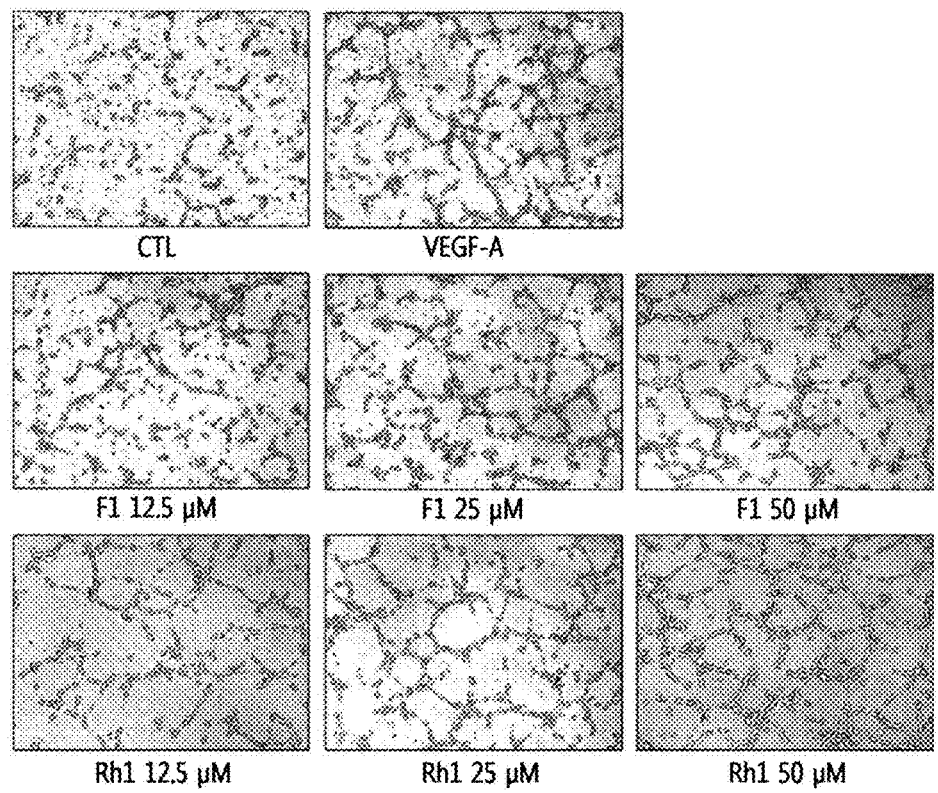

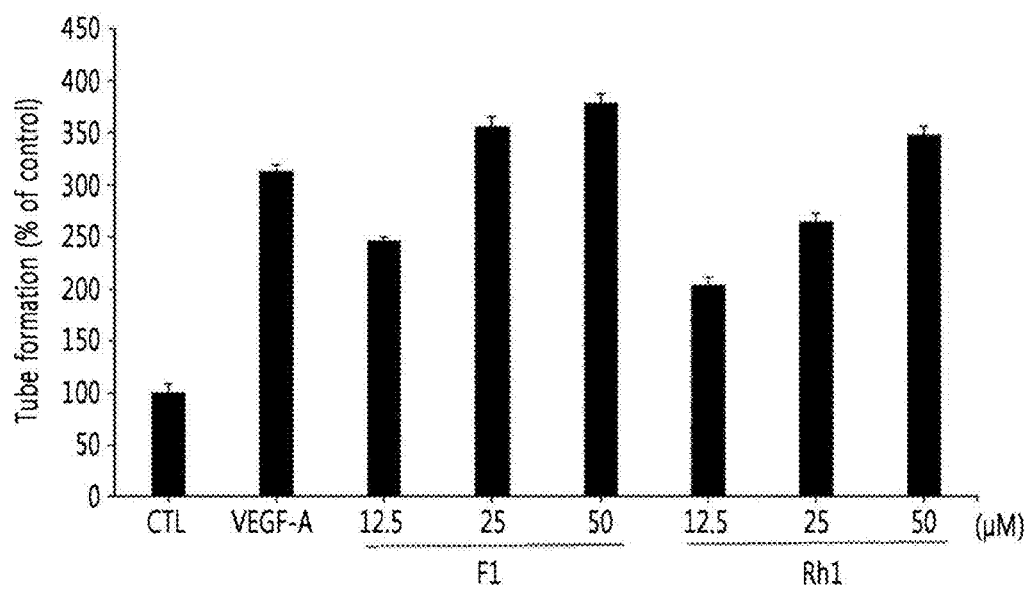

[FIG. 4A]
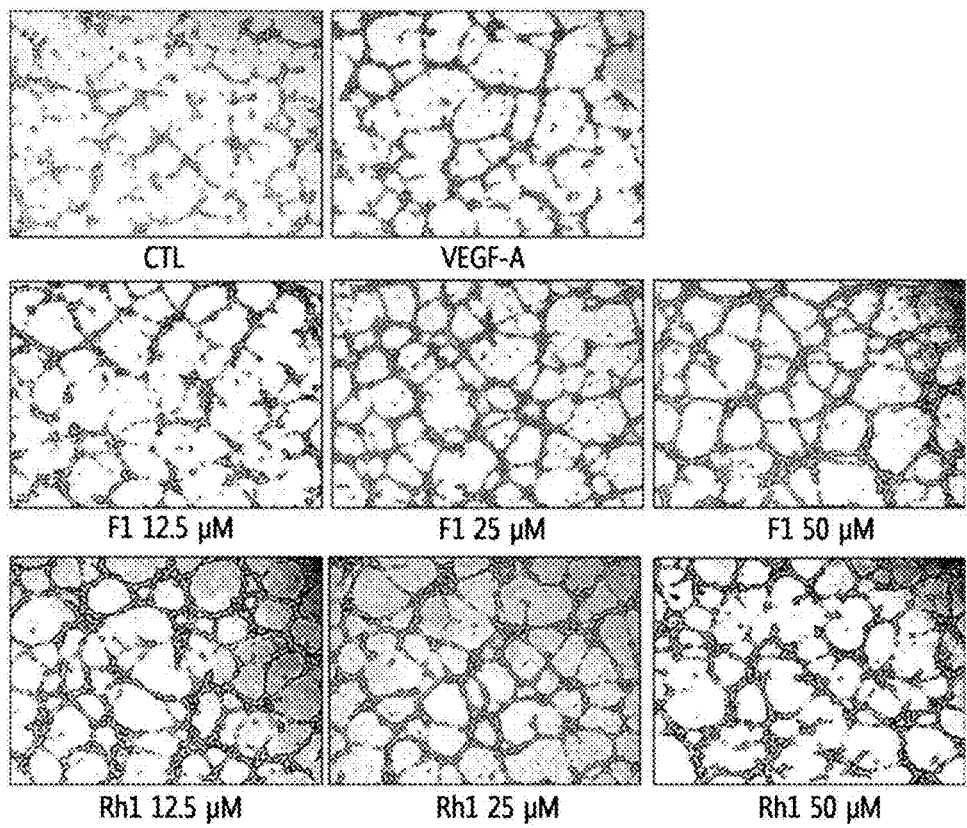

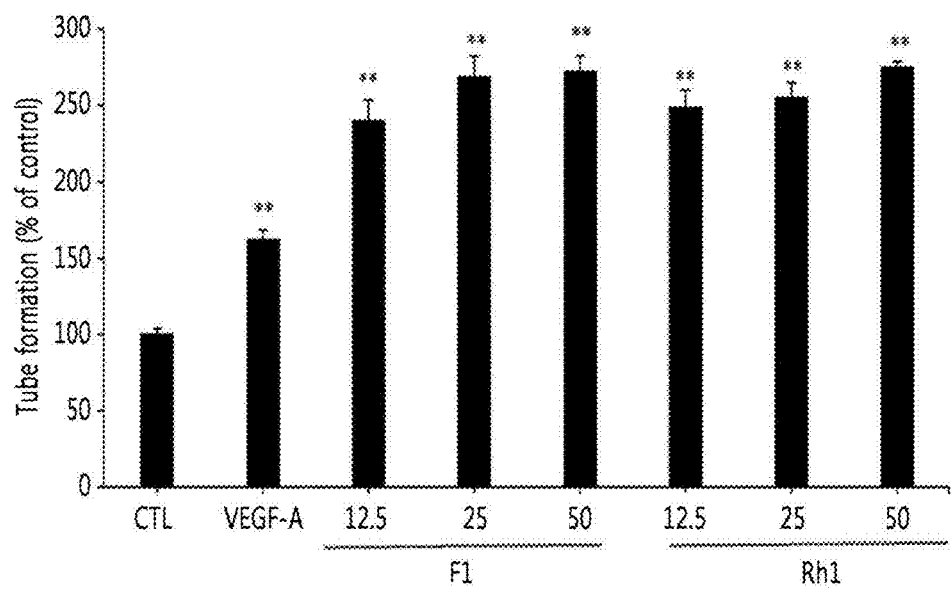
[FIG. 4B]

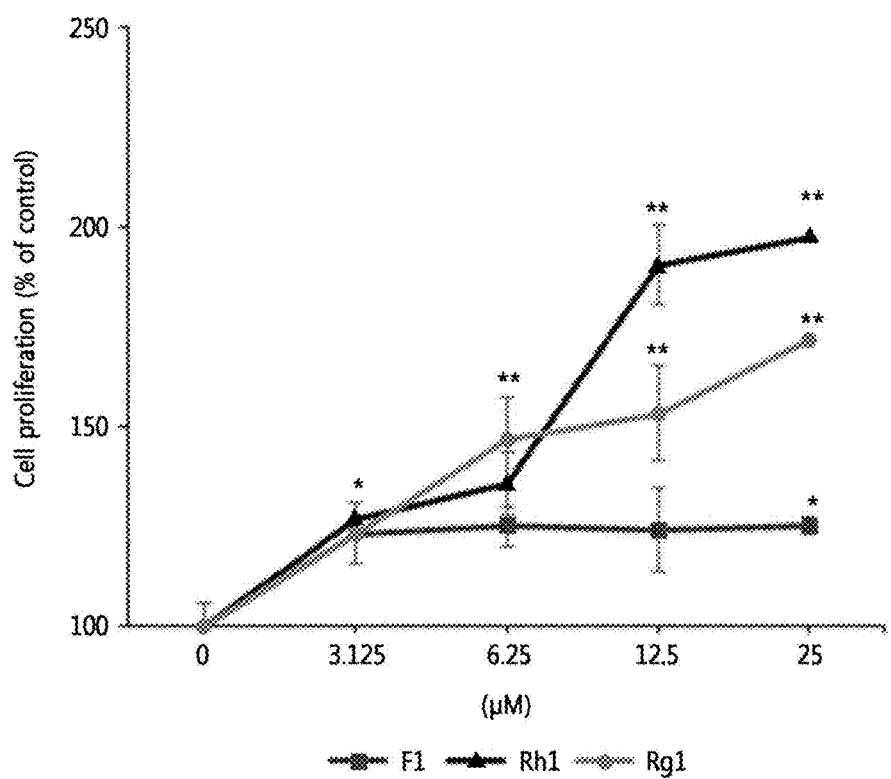

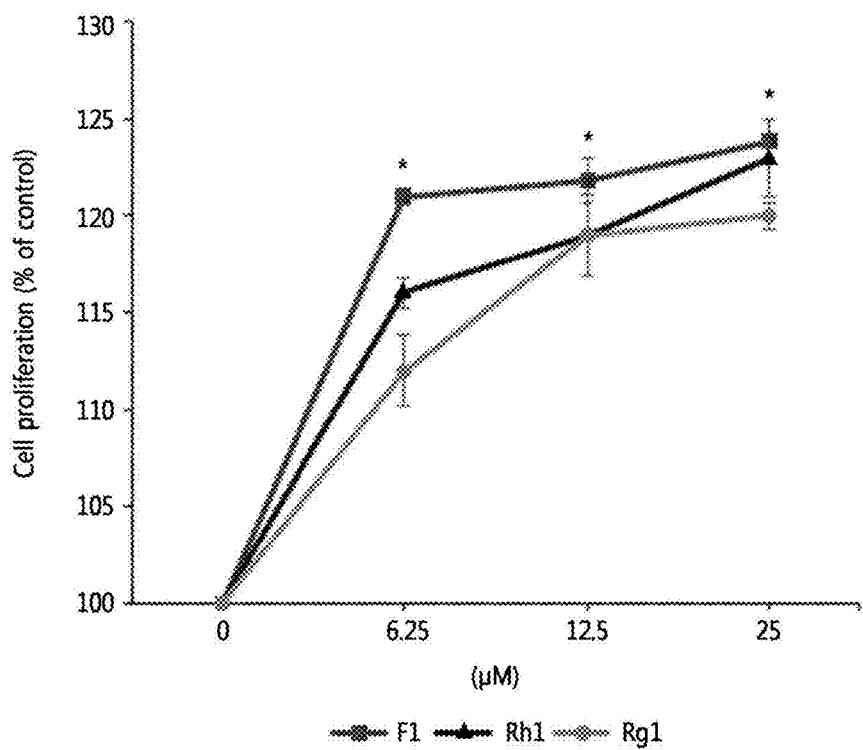
[FIG. 6]

[FIG. 7A]
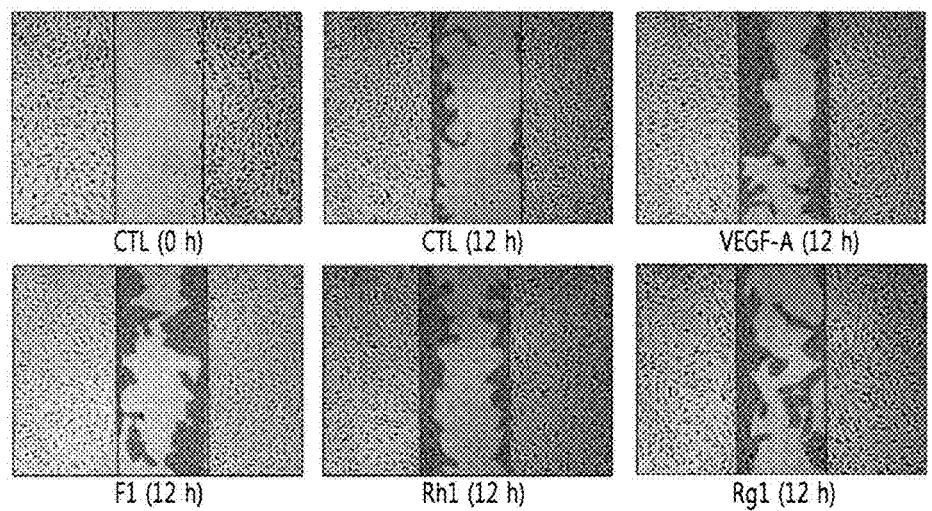
[FIG. 7B]
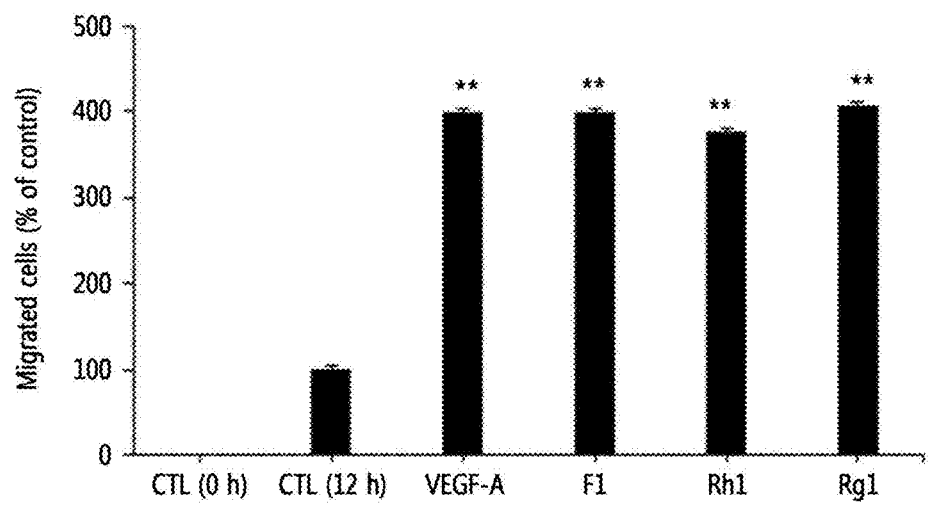

[FIG. 8A]
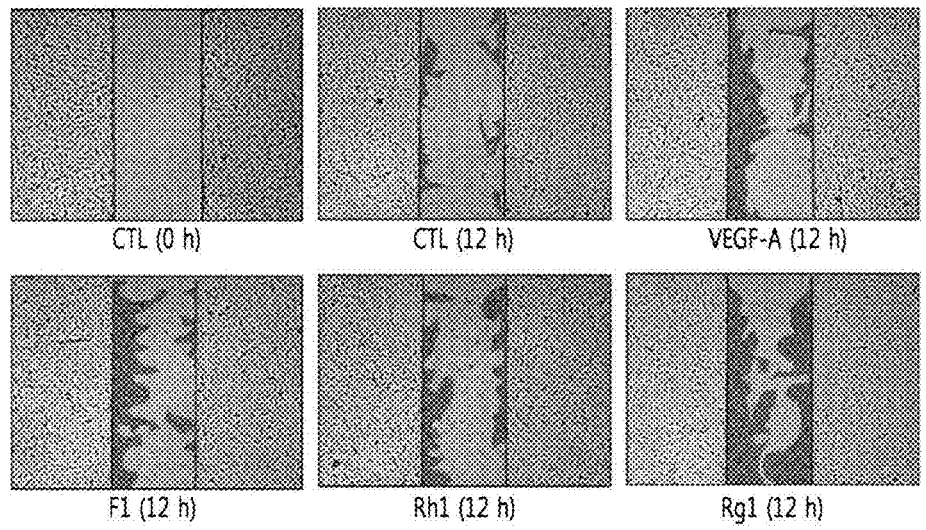
[FIG. 8B]
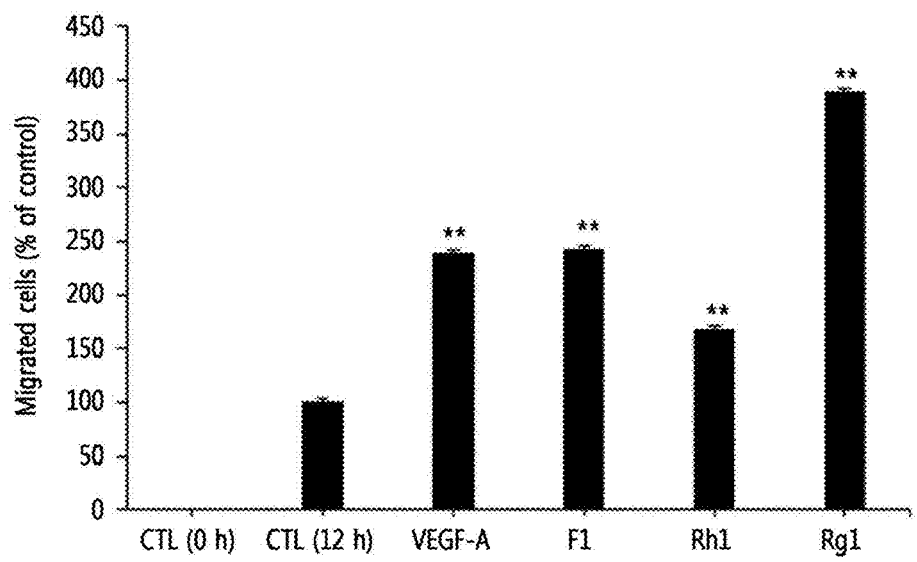

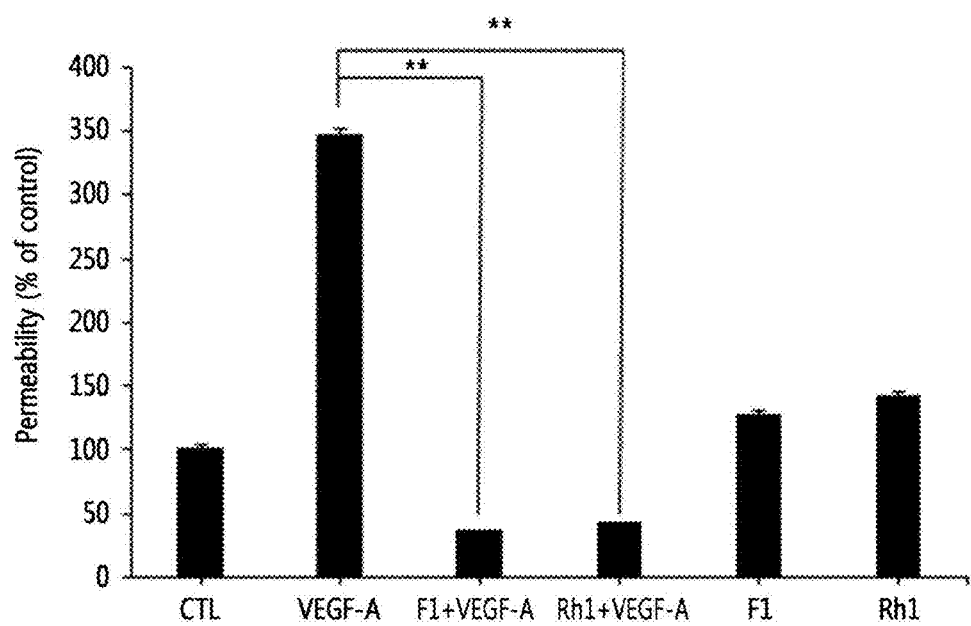
[FIG. 9]

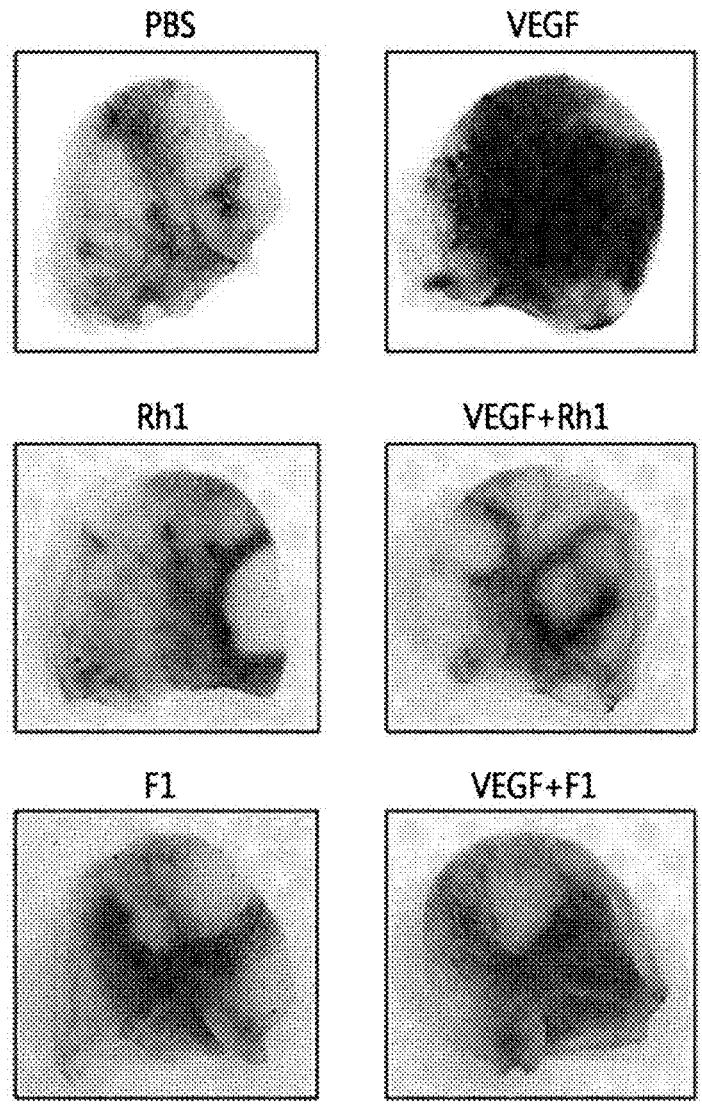
[FIG. 10A]

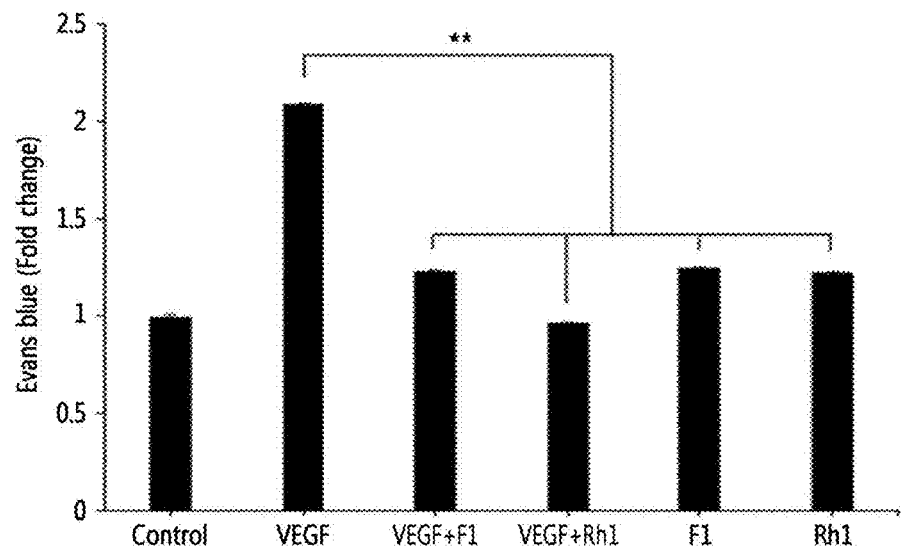
[FIG. 10B]

COMPOSITION FOR PREVENTING OR TREATING VASCULAR LEAK SYNDROME

This application is a national phase application under 35 U.S.C. § 371 of International Application No. PCT/KR2016/005318, filed May 19, 2016, which claims priority to Korean Application No. 10-2015-0101239, filed Jul. 16, 2015. The entire text of each of the above referenced disclosures is specifically incorporated herein by reference.

TECHNICAL FIELD

The present invention relates to a composition for preventing or treating vascular leak syndrome, and more specifically, to a pharmaceutical composition for preventing or treating vascular leak syndrome containing ginsenoside F1 or Rh1, a method for treating vascular leak syndrome using the pharmaceutical composition, and a food composition containing ginsenoside F1 or Rh1 for preventing or ameliorating vascular leak syndrome.

BACKGROUND ART

Cross-sections of vascular walls show an asymmetrical structure, which consists of tunica intima consisting of endothelium; connective tissues consisting of elastin, collagen fibers, etc.; tunica media consisting of smooth muscles; and tunica adventitia consisting of collagen fiber layer. The asymmetrical structure of blood vessels is known to inhibit thrombosis, prevent vascular leakage, and provide fluidity of blood vessels. Specifically, in "tunica intima" consisting of vascular endothelium, polymers of sugar components are accumulated on the surface and form a glycocalyx layer, which has the roles of directly controlling the blood flow and preventing the direct contact between blood and epithelial cells, thereby inhibiting the entrance of blood components into epithelial cells. In addition, the glycocalyx layer is known to be involved in various physiological activities such as the regulation of blood vessel tone, exchange of fluids and solutes between blood and tissue, leukocyte migration, hemostasis and blood coagulation, inflammatory responses, etc.

It is known that once the glycocalyx layer is damaged, it firstly results in the loss of vascular function, and secondly, physiologically activities related to blood vessels are inhibited. The most serious effect caused by the damage in the glycocalyx layer is the functional loss of blood vessels, and once the glycocalyx layer is damaged by mechanical stimulation such as wounds, surgeries, etc., the components in the blood may escape through the epithelial cells to the outside of the blood vessels. Such a symptom where the components in the blood flow out of the blood vessels is called vascular leakage. The blood leakage may be induced by excess oxygen radicals, in addition to the mechanical stimulation described above, and may also be induced by various diseases such as ulcer of gastric organs, internal bleeding, inflammation, ischemia, diabetes, etc.

The representative example of the diseases which induce blood leakage may be vascular leak syndrome. The vascular leak syndrome is a disease where blood plasma is leaked through the vascular wall by extravasation and thereby induces edema of neighboring tissues. In general, vascular leak syndrome is known to occur as a side-effect of treatments using interleukin-2. However, since vascular leak syndrome is known to not occur in all of the patients who received the treatment using interleukin-2, a possibility was raised that the syndrome may occur due to genetic reasons of individual patients, and thus vascular leak syndrome is also considered as a kind of a genetic disease. However, since it is not easy to obtain samples of patients induced with vascular leak syndrome, there was a problem in that it was not easy to study vascular leakage symptoms via vascular leak syndrome. As such, as an alternative to patients with vascular leak syndrome, various studies were performed in diabetic patients with frequent vascular leakage. As a result, it was found that vascular leakage is induced by overexpression of vascular endothelial growth factor (VEGF). That is, it was reported that the VEGF overexpression induced at the onset of diabetes can decompose VE-cadherin, which has an important role of maintaining the binding between epithelial cells, and decreases the binding between epithelial cells and induces the damage of glycocalyx layer, thereby causing the occurrence of vascular leakage. Additionally, the vascular leakage may be induced by a surgical process for the treatment of cardiovascular disease. For example, as a method for treating an aneurysm, which is a disease where part of an artery expands when the artery wall weakens or the inner pressure of the artery increases, a surgical method of inserting an prosthesis such as a stent between blood vessels where an aneurysm occurred is being used for preventing a further influx of a blood flow into the expanded area, and vascular leakage may occur in the neighboring region of the stent. Such vascular leakage occurring during the treatment of an aneurysm is also called "endoleak", and when endoleak occurs, there is a problem in that a second surgery is needed. Such vascular leakage basically causes the loss of blood, lowers blood pressure, etc., and as a result, a secondary damage due to anemia or ischemia may be induced. Accordingly, active studies have been focused on the development of a method for effective treatment of vascular leakage.

For example, International Patent Publication No. WO 2010/081172 discloses compounds that prevent vascular leakage; Korean Patent No. 958578 discloses a stent that can prevent vascular leakage during the treatment of aneurysm; Korean Patent No. 1239495 discloses a method for treating diabetic retinopathy using recombinant adenovirus which expresses αA-crystallin gene; and International Patent Publication No. WO 2014/025127 discloses a C-peptide which can suppress vascular leakage by inhibiting the VEGF-induced VE-cadherin degradation. However, among the developed technologies above, the use of the stent can be limited to the treatment of arteries only, and there is a possibility that compounds or C-peptide can cause a side effect. Therefore, there is a need for the development of a formulation for safer and more effective treatment of vascular leakage.

DISCLOSURE

Technical Problem

The present inventors have made extensive efforts for the development of a preparation which can safely and effectively treat vascular leak syndrome. As a result, the inventors have confirmed that various ginsenoside compounds derived from ginseng exhibit an effect of treating vascular leakage effectively, and among them, ginsenoside F1 or Rh1 exhibits the most excellent effect of treating vascular leakage, thereby completing the present invention.

Technical Solution

An object of the present invention is to provide a pharmaceutical composition for preventing or treating vascular leak syndrome, containing ginsenoside F1 or Rh1.

Another object of the present invention is to provide a method for treating vascular leak syndrome using the pharmaceutical composition.

A further object of the present invention is to provide a food composition for preventing or ameliorating vascular leak syndrome, containing ginsenoside F1 or Rh1.

Advantageous Effects of the Invention

The ginsenoside F1 or Rh1 provided in the present invention not only can promote angiogenesis and but also suppress vascular leakage, and thus can be widely utilized in the effective prevention or treatment of vascular leak syndrome.

BRIEF DESCRIPTION OF DRAWINGS

FIG. 1A shows the images of HUVECs cultured by treating with 10 kinds of ginsenosides.

FIG. 1B shows the graph illustrating the comparison results with regard to the number of tubes formed in the HUVECs cultured by treating with 10 kinds of ginsenosides.

FIG. 2A shows the images of HRMECs cultured by treating with 10 kinds of ginsenosides.

FIG. 2B shows the graph illustrating the comparison results with regard to the number of tubes formed in the HRMECs cultured by treating with 10 kinds of ginsenosides.

FIG. 3A shows the images of HUVECs cultured by treating with F1 and Rh1 at various concentrations.

FIG. 3B shows the graph illustrating the comparison results with regard to the number of tubes formed in the HUVECs cultured by treating with F1 and Rh1 at various concentrations.

FIG. 4A shows the images of HRMECs cultured by treating with F1 and Rh1 at various concentrations.

FIG. 4B shows the graph illustrating the comparison results with regard to the number of tubes formed in the HRMECs cultured by treating with F1 and Rh1 at various concentrations.

FIG. 5 shows the graph illustrating the comparison results with regard to the proliferation level of HUVECs cultured by treating with 3 kinds of ginsenosides at various concentrations (0, 3.125, 6.25, 12.5, or 25 µM).

FIG. 6 shows the graph illustrating the comparison results with regard to the proliferation level of HRMECs cultured by treating with 3 kinds of ginsenosides at various concentrations (0, 6.25, 12.5, or 25 µM).

FIG. 7A shows the images illustrating the results of cell migration assay of HUVECs cultured by treating with 3 kinds of ginsenosides at various concentrations.

FIG. 7B shows the graph illustrating the comparison results of the percentage of migrated cells obtained by cell migration assay of HUVECs cultured by treating with 3 kinds of ginsenosides at various concentrations.

FIG. 8A shows the images illustrating the results of cell migration assay of HRMECs cultured by treating with 3 kinds of ginsenosides at various concentrations.

FIG. 8B shows the graph illustrating the comparison results of the percentage of migrated cells obtained by cell migration assay of HUVECs cultured by treating with 3 kinds of ginsenosides at various concentrations.

FIG. 9 shows the graph illustrating the comparison results with regard to the effect of the –ginsenoside F1 or Rh1 on vascular leakage induced by treating HUVECs with VEGF-A.

FIG. 10A shows the images illustrating the effects of ginsenosides F1 or Rh1 on vascular leak syndrome induced by VEGF-A in mouse ears, confirmed by the naked eye by Evans blue staining.

FIG. 10B shows the graph illustrating the effects of ginsenosides F1 or Rh1 on vascular leak syndrome induced by VEGF-A in mouse ears, confirmed by a quantitative analysis at the level of Evans blue staining.

BEST MODE

While performing various studies to develop therapeutic agents for the effective prevention or treatment of vascular leak syndrome with improved safety, the present inventors have paid attention to ginsenosides. The ginsenoside compounds are kinds of compounds contained in ginseng or red ginseng, and they are known to have therapeutic effects on various diseases accompanying angiogenesis or vascular damage. Therefore, attempts were made to select ginsenosides which exhibit the most effective therapeutic effect for vascular leak syndrome. As a result, ginsenosides Rh1 and F1 were selected as the ginsenosides which can promote tube formation at an excellent level with regard to the human umbilical vascular endothelial cells (HUVECs) and human retinal microvascular endothelial cells (HRMECs), which are endothelial cells, similar to the vascular endothelial cells. As a result of confirming the effects of the selected ginsenosides Rh1 and F1, it was confirmed that the ginsenosides were able to promote angiogenesis, cell proliferation, cell migration, and inhibit vascular leakage, in a concentration-dependent manner.

The inhibitory effect of ginsenosides F1 or Rh1 against vascular leakage had not been reported previously and the present inventors are the first to confirm the effect.

In order to achieve the above objects, in an aspect, the present invention provides a pharmaceutical composition for preventing or treating vascular leak syndrome, containing ginsenoside F1 or Rh1.

As used herein, the term "ginsenoside F1", also called 20-O-β-D-glucopyranosyl-20(S)-protopanaxatriol, refers to a compound having the structure of the following Formula 1, which is indicated as the formula of $C_{36}H_{62}O_9$, has a molecular weight of about 638.87 Da, and is isolated from ginseng.

[Formula 1]

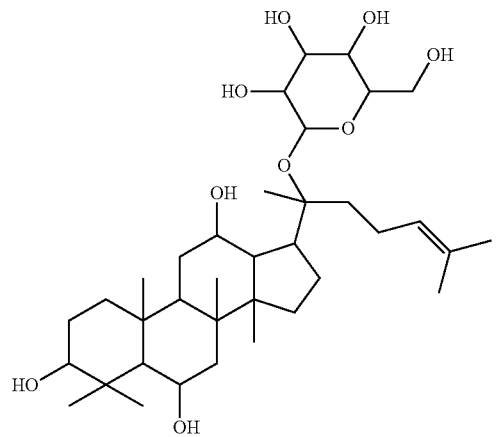

In the present invention, the ginsenoside F1 may be used as an active ingredient of the pharmaceutical composition for preventing or treating diseases accompanying vascular leakage.

As used herein, the term "ginsenoside Rh1", also called 6-O-β-D-glucopyranoside-20(S)-protopanaxatriol, refers to a compound having the structure of the following Formula 2, which is indicated as the formula of $C_{36}H_{62}O_9$, has a molecular weight of about 638.87 Da, and is isolated from ginseng.

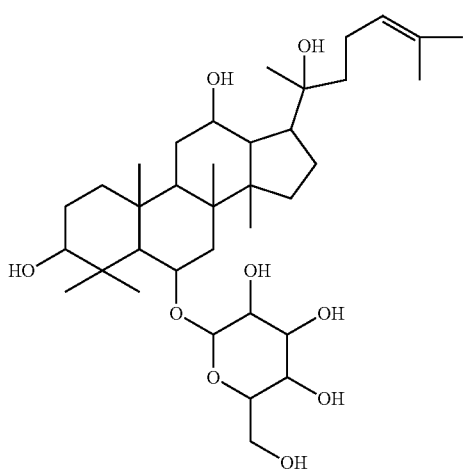

[Formula 2]

In the present invention, ginsenoside Rh1 may be used as an active ingredient of the pharmaceutical composition for preventing or treating diseases accompanying vascular leakage.

As used herein, the term "vascular leak syndrome (also called vascular leakage syndrome)" refers to a disease which causes interstitial edema of neighboring tissues by vascular leak syndrome, where blood plasma is leaked to the outside of the blood vessels by the extravasation through vascular walls. Generally, vascular leak syndrome occurs as a side-effect of treatments using interleukin 2, and its occurrence is known to be determined by genetic factors. In addition, VEGF which secreted in a morbid stat, such as cancer and cardiovascular diseases can induces vascular leakage.

As used herein, the term "vascular leakage" refers to a symptom that the components in the blood move out of the blood vessel due to the increased permeability of a blood vessel wall by various reasons, such as damage of a glycocalyx layer in vascular endothelial cells, loss of binding affinity of vascular endothelial cells, etc., among the blood vessel-forming components, and the symptom may be usually diagnosed indirectly via low blood pressure, peripheral edema, hypoalbuminemia, etc. Although the vascular leakage is the major symptom of vascular leak syndrome, blood leakage may be induced by excess oxygen radicals and mechanical stimulation that directly damage the constituting components of the blood, in addition to the vascular leak syndrome, and may also be induced by various diseases such as ulcer of gastric organs, internal bleeding, inflammation, ischemia, diabetes, etc.

According to an embodiment, for the selection of ginsenosides exhibiting an angiogenesis-promoting activity, the ginsenosides exhibiting an excellent angiogenesis-promoting activity were selected from HUVECs and HRMECs among the 10 kinds of ginsenoside compounds (CK, Rh2, Rg3, Rb1, F2, Rd, Re, Rg1, Rh1, or F1). As a result, the ginsenosides exhibiting the effect of promoting tube formation at high level were confirmed to be ginsenoside F1 or Rh1 (FIGS. 1 and 2). When these ginsenosides were treated on HUVECs, it was confirmed that the HUVECs exhibited an effect of promoting tube formation in a concentration-dependent manner (FIG. 3), an effect of promoting the cell proliferation of HUVECs and HRMECs (FIGS. 5 and 6), an effect of promoting the cell migration of HUVECs and HRMECs (FIGS. 7 and 8), an effect of suppressing the level of vascular leakage induced by treating the HUVECs with VEGF-A (FIG. 9), and an effect of suppressing the level of vascular leakage induced by treating with VEGF-A at a cellular level (FIG. 9) and at an animal level (FIGS. 10A and 10B).

Accordingly, it was confirmed that ginsenosides F1 or Rh1 not only have an effect of promoting angiogenesis but also an effect of suppressing vascular leakage, and these effects were exhibited at an animal level as well as at a cellular level thus confirming that ginsenosides F1 or Rh1 can be used as therapeutic agents for preventing or treating diseases accompanying vascular leakage.

In particular, it is known that VEGF is secreted in a morbid state, such as cancer and cardiovascular diseases, and induces vascular leakage and also plays an important role of forming abnormal blood vessels. Since the ginsenosides F1 or Rh1 provided in the present invention can suppress vascular leakage while simultaneously forming blood vessels, the ginsenosides F1 or Rh1 are thought to exhibit a new effect of forming normal new blood vessels.

Accordingly, the ginsenosides F1 or Rh1 provided in the present invention are expected to be used not only for the treatment of various ischemic diseases, where the formation of blood vessels is suppressed, but also for the treatment of cancer and cardiovascular disease, where the normal functions of blood vessels are lost and abnormal blood vessels are formed due to the secretion of VEGF.

Meanwhile, the composition of the present invention may be prepared in the form of a pharmaceutical composition for preventing or treating vascular leak syndrome, which further contains an appropriate carrier, excipient, or diluent conventionally used for the preparation of pharmaceutical compositions, and the carrier may be non-naturally occurring. Specifically, the pharmaceutical composition may be prepared for use in the form of oral formulations such as powders, granules, tablets, capsules, suspensions, emulsions, syrups, aerosols, etc.; formulations for external use; suppositories; and sterile injections, according to the conventional methods, respectively. In the present invention, the carrier, excipient, or diluent to be contained in the pharmaceutical composition may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, mineral oil, etc. The formulations may be prepared using a diluent or excipient, such as a filler, an extender, a binder, a humectant, a disintegrant, a surfactant, etc. Solid formulations for oral administration may include tablets, pills, powders, granules, capsules, etc., and these solid formulations may be prepared by adding at least one excipient, e.g., starch, calcium carbonate, sucrose or lactose, gelatin, etc., to the extract and fractions thereof. Additionally, a lubricant, such as magnesium stearate, talc, etc., may be used, in addition to the simple excipient. Liquid formulations for oral administration may include suspensions, liquid medicines for internal use, emulsions, syrups, etc., and various excipients, such as humectants, sweeteners, fragrances, preservatives, etc., may be used, in addition to the simple diluents such as water and liquid paraffin. Formulations for parenteral administration may include sterilized aqueous solutions, non-aqueous solvents, suspensions, emulsions, lyophilized formulations, and suppositories. Examples of the non-aqueous solvents and suspensions may include propylene glycol, polyethylene glycol, and vegetable oils such as olive oil, an injectable ester such as ethyl oleate, etc. Examples of the bases for suppositories may include Witepsol, macrogol, Tween 61, cacao butter, laurinum, glycerogelatin, etc.

The amount of ginsenoside F1 or ginsenoside Rh1 contained in the pharmaceutical composition of the present invention, in an exemplary embodiment, may be in an amount of 0.0001 wt % to 50 wt %, and more preferably 0.01 wt % to 10 wt %, based on the total amount of the final composition, but is not particularly limited thereto.

The pharmaceutical composition of the present invention may be administered in a pharmaceutically effective amount. As used herein, the term "pharmaceutically effective amount" refers to an amount sufficient for the treatment of diseases at a reasonable benefit/risk ratio applicable to a medical treatment or prevention, and the level of the effective dose may be determined based on the factors including severity of illness, drug activity, age, body weight, health conditions, sex, drug sensitivity of a patient, administration time, administration route, excretion rate, and length of treatment of the composition used in the present invention, factors including drug(s) to be concurrently used in combination with the composition of the present invention, and other factors well-known in the medical field. The pharmaceutical composition of the present invention may be administered alone or in combination with other known therapeutic agent(s) for preventing or treating vascular leak syndrome. It is important to administer an amount to obtain the maximum effect with a minimum amount without adverse effects considering the factors described above.

The administration dose of the pharmaceutical composition of the present invention may be determined by one or ordinary skill in the art considering the purpose of use, severity of disease, age, body weight, sex, anamnesis of a patient, or a kind of material(s) to be used as an active ingredient, etc. For example, the pharmaceutical composition of the present invention may be administered in an amount of about 0.1 ng to 100 mg/kg, and more preferably 1 ng/kg to 10 mg/kg per adult, and the frequency of administration of the pharmaceutical composition of the present invention may be administered once daily or several times in divided doses a day, but is not particularly limited thereto. The administration dose is not intended to limit the scope of the present invention in any manner.

Another aspect of the present invention provides a method for preventing or treating vascular leak syndrome including administering a pharmaceutically effective amount of the pharmaceutical composition to a subject having a risk of the occurrence of vascular leak syndrome or a subject with vascular leak syndrome.

As used herein, the term "subject" may include without limitation mammals, which include rats, cattle, humans, etc., farming fishes, etc., having a risk of the occurrence of vascular leak syndrome or a subject with vascular leak syndrome.

The pharmaceutical composition of the present invention for preventing or treating vascular leak syndrome may be administered by any general route as long as it can arrive at the target tissue. The pharmaceutical composition of the present invention may be administered intraperitoneally, intravenously, intramuscularly, subcutaneously, intradermally, orally, intranasally, intrapulmonarily, intrarectally, etc., but the administration route is not particularly limited thereto. However, since ginsenoside F1 or Rh1 may be denatured by gastric acid in case of an oral administration, the active drug ingredient of the composition for oral administration may be coated or the composition may be formulated to be protected from decomposition. Additionally, the composition may be administered by any device that can deliver the active ingredient to the target cells.

Still another aspect of the present invention provides a food composition for preventing or ameliorating vascular leak syndrome containing ginsenoside F1 or Rh1.

Since ginsenoside F1 or Rh1, the active ingredients of the pharmaceutical composition for preventing or treating vascular leak syndrome, are compounds derived from natural herbal substances such as ginseng, etc., whose safety has been proved as they have been used as herbal medicine from the ancient times, they can be prepared to be eaten in the form of foods for promoting the effect of preventing or treating vascular leak syndrome.

In particular, although the amount of ginsenoside F1 or Rh1 to be contained in the food is not particularly limited, it may preferably be contained in an amount of 0.001 wt % to 50 wt %, and more preferably 0.1 wt % to 10 wt %, based on the total weight of the food composition. When the food is a beverage it may be contained in an amount of 1 g to 10 g, and preferably 2 g to 7 g, based on 100 mL. Additionally, the composition may contain additional ingredient that is conventionally used in food compositions so as to improve smell, taste, vision, etc. For example, the composition may contain vitamins A, C, D, E, B1, B2, B6, B12, niacin, biotin, folate, pantothenic acid, etc. Additionally, the composition may also contain minerals such as Zn, Fe, Ca, Cr, Mg, Mn, Cu, etc. Additionally, the composition may also contain amino acids such as lysine, tryptophan, cysteine, valine, etc. Additionally, the composition may also contain food additives, such as preservatives (potassium sorbate, sodium benzoate, salicylic acid, sodium dehydroacetate, etc.), disinfectants (bleaching powder, higher bleaching powder, sodium hypochlorite, etc.), antioxidants (butylhydroxyanisole (BHA), butylhydroxytoluene (BHT), etc.), coloring agents (tar color, etc.), color-developing agents (sodium nitrite, etc.), bleaching agents (sodium sulfite), seasonings (monosodium glutamate (MSG), etc.), sweeteners (dulcin, cyclemate, saccharin, sodium, etc.), flavors (vanillin, lactones, etc.), swelling agents (alum, potassium D-hydrogen tartate, etc.), fortifiers, emulsifiers, thickeners (adhesive pastes), film-forming agents, gum base agents, antifoaming agents, solvents, improvers, etc. The additives may be selected and used in an appropriate amount according to the food types.

Meanwhile, a health functional food for preventing or ameliorating vascular leak syndrome may be prepared using a food composition for preventing or ameliorating vascular leak syndrome containing ginsenoside F1 or Rh1.

In a specific embodiment, processed foods for preventing or ameliorating vascular leak syndrome may be prepared using the food composition. For example, a health functional food may be prepared in the form of confectioneries, beverages, alcohols, fermented foods, canned foods, milk processed foods, meat-processed foods, or noodle-processed foods. In particular, confectioneries may include biscuits, pies, cakes, breads, candies, jellies, gums, cereals (meal substitutes such as grain flakes, etc.), etc. Examples of beverages may include drinking water, carbonated drinks, functional ion drinks, juices (e.g., apple, pear, grape, aloe, tangerine, peach, carrot, tomato juices, etc.), sweet rice drinks, etc. Examples of alcohols may include refined rice wine, whiskey, soju, beer, liquor, fruit wine, etc. Examples of fermented foods may include soy sauce, soybean paste, red pepper paste, etc. Examples of canned foods may include canned marine products (e.g., canned products of tuna, mackerel, pacific saury, conch, etc.), canned meat products (canned products of beef, pork, chicken, turkey, etc.), canned agricultural products (canned products of corn, peach, pineapple, etc.), etc. Examples of milk-processed products may include cheese, butter, yogurt, etc. Examples of meat-processed foods may include pork cutlet, beef cutlet, chicken cutlet, sausage, sweet-and-sour pork, nuggets, Neobiani, etc. Noodles such as sealing-packed wet noodles may be included. Additionally, the food composition may be used in retort foods, soups, etc.

As used herein, the term "functional food", being the same term as food for special health use (FoSHU), refers to a food with high medicinal and medical effects to efficiently exhibit a bioregulatory function in addition to a function of nutrient supply. The functional food may be prepared in various forms such as tablets, capsules, powders, granules, liquids, pills, etc., to obtain useful effects for preventing or ameliorating vascular leak syndrome.

DETAILED DESCRIPTION OF THE INVENTION

Hereinafter, the present invention will be described in more detail with reference to the following Examples. However, these Examples are for illustrative purposes only, and the invention is not intended to be limited by these Examples.

Example 1: Selection of Ginsenosides Exhibiting Angiogenesis-Promoting Activities The angiogenesis-promoting activities between human umbilical vascular endothelial cells (HUVECs) and human retinal microvascular endothelial cells (HRMECs) using 10 kinds of ginsenoside compounds (CK, Rh2, Rg3, Rb1, F2, Rd, Re, Rg1, Rh1, or F1). That is, HUVECs or HRMECs were cultured in an incubator (5% $CO_2$ and 37° C.) using 2% FBS, EGM-2 (Lonza, Walkersville, Md., USA) medium. A 96-well plate was coated with Matrigel (BD Biosciences) for 1 hour. Then, HUVECs or HRMECs ($10^4$ cells/well, respectively), which were mixed with a 0.1% FBS-containing EBM-2 medium respectively treated with 25 μM of ginsenoside compounds (CK, Rh2, Rg3, Rb1, F2, Rd, Re, Rg1, Rh1, or F1), were seeded on the 96-well plate. After 4 hours of incubation, a tube formation assay was performed and the number of tubes formed was compared by microscopic observation and photographing (FIGS. 1a, 1b, 2a, and 2b). In particular, the cells cultured after treating with DMSO instead of ginsenoside were used as a negative control, and the cells cultured after treating with VEGF-A, which is known to promote angiogenesis, were used as a positive control.

First, FIG. 1A shows the images of HUVECs cultured by treating with 10 kinds of ginsenosides, and FIG. 1B shows the graph illustrating the comparison results with regard to the number of tubes formed in the HUVECs cultured by treating with 10 kinds of ginsenosides. As can be seen in FIG. 1, it was confirmed that, during the cultivation of HUVECs, ginsenoside CK, Rb2, or Rg3 showed an effect of inhibiting tube formation; ginsenoside Rb1 or F2 did not show any noticeable difference; and ginsenoside Rd, Re, Rg1, Rh1, or F1 showed an effect of promoting tube formation.

Next, FIG. 2A shows the images of HRMECs cultured by treating with 10 kinds of ginsenosides, and FIG. 2B shows the graph illustrating the comparison results with regard to the number of tubes formed in the HRMECs cultured by treating with 10 kinds of ginsenosides. As can be seen in FIG. 2, it was confirmed that, during the cultivation of HRMECs, ginsenoside CK, Rb2, or Rg3 showed an effect of inhibiting tube formation and ginsenoside Re, Rb1, Rg1, Rd, F1, gF2, or Rh1 showed an effect of promoting tube formation.

Additionally, it was confirmed that the ginsenosides which commonly showed the effect of promoting tube formation both in culturing HUVECs or HRMECs were Re, Rd, F1, or Rh1, and among them, the ginsenosides which showed an effect of promoting tube formation at a higher level compared to that of the positive control were ginsenosides F1 or Rh1.

Accordingly, ginsenosides F1 or Rh1 were selected and used for subsequent experiments.

Example 2: Angiogenesis-Promoting Effect According to Ginsenoside Treatment at Various Concentrations The HUVECs or HRMECs, which were cultured by the method of Example 1, were cultured after treating at various concentrations (12.5, 25, or 50 μM) of ginsenoside F1 or Rh1 selected from Example 1 for 4 hours, and the number of tubes formed was compared by performing a tube formation assay (FIGS. 3 and 4). In particular, the cells cultured after treating with DMSO instead of ginsenoside were used as a negative control and the cells cultured after treating with VEGF-A, which is known to promote angiogenesis, were used as a positive control.

FIG. 3A shows the images of HUVECs cultured by treating with 2 kinds of ginsenosides at various concentrations, and FIG. 3B shows the graph illustrating the comparison results with regard to the number of tubes formed in the HUVECs cultured by treating with the 2 kinds of ginsenosides at various concentrations. As can be seen in FIG. 3, it was confirmed that, during the cultivation of HUVECs, both of the 2 kinds of ginsenosides promoted tube formation in a concentration-dependent manner, and the treatment with 50 μM, the 2 kinds of ginsenosides formed tubes at a higher level compared to that of the positive control.

FIG. 4A shows the images of HRMECs cultured by treating with 2 kinds of ginsenosides at various concentrations, and FIG. 4B shows the graph illustrating the comparison results with regard to the number of tubes formed in the HRMECs cultured by treating with the 2 kinds of ginsenosides at various concentrations. As can be seen in FIG. 4, it was confirmed that, during the cultivation of HRMECs, 2 kinds of ginsenosides did not distinctively show the effect of promoting tube formation in a concentration-dependent manner; however, the 2 kinds of ginsenosides showed a higher level of tube formation compared to that of the positive control at all concentrations.

Example 3: Cell Proliferation-Promoting Effect According to Ginsenoside Treatment at Various Concentrations The HUVECs or HRMECs, which were cultured by the method of Example 1, were cultured after treating at various concentrations (0, 3.125, 6.25, 12.5, or 25 μM) of three kinds of ginsenosides (F1, Rh1, or Rg1), which were confirmed to promote tube formation in Example 1, for 48 hours, and the level of cell proliferation was compared by performing the MTT assay with respect to the cultured cells (FIGS. 5 and 6). In particular, the cells cultured after treating with DMSO instead of ginsenoside were used as a negative control, and the cells cultured after treating with VEGF-A, which is known to promote angiogenesis, were used as a positive control.

FIG. 5 shows the graph illustrating the comparison results with regard to the proliferation level of HUVECs cultured by treating with 3 kinds of ginsenosides at various concentrations (0, 3.125, 6.25, 12.5, or 25 μM). As can be seen in FIG. 5, it was confirmed that, during the cultivation of HUVECs, ginsenoside F1 showed a promotion of about 20% of cell proliferation; ginsenoside Rh1 showed a promotion of about 100% of cell proliferation; and ginsenoside Rg1 showed a promotion of about 60% of cell proliferation.

FIG. 6 shows the graph illustrating the comparison results with regard to the proliferation level of HRMECs cultured by treating with 3 kinds of ginsenosides at various concentrations (0, 6.25, 12.5, or 25 μM). As can be seen in FIG. 6, it was confirmed that, during the cultivation of HRMECs, it was confirmed that all of the 3 kinds of ginsenosides showed a promotion of about 20% of cell proliferation.

Example 4: Cell Migration-Promoting Effect of Ginsenosides

To examine the effect of the 3 kinds of ginsenosides, which were confirmed to promote tube formation in Example 1, with respect to the cell migration of HUVECs or HRMECs, a cell migration assay was performed.

Specifically, a culture container provided with a culture-insert (a culture-insert of μ-dish, Ibidi) was coated with 0.1% gelatin, and EGM-2 medium was added thereto. Then, the HUVECs or HRMECs, which were cultured by the method of Example 1, were inoculated and cultured up to 90% of degree of saturation, and the insert was removed. Then, the medium was replaced with EBM-2 medium which contained 25 μM of 3 kinds of ginsenosides (F1, Rh1, or Rg1) and 0.1% FBS, cultured again for 12 hours, and the level of cell migration of HUVECs or HRMECs was analyzed under a microscope (FIGS. 7A, 7B, 8A, and 8B). In particular, the cells cultured for 12 hours after treating with DMSO instead of ginsenoside were used as a negative control, and the cells cultured for 12 hours after treating with VEGF-A, which is known to promote angiogenesis, were used as a positive control, and uncultured cells were used as a reference control.

FIG. 7A shows the images illustrating the results of performing cell migration assay of HUVECs cultured by treating with 3 kinds of ginsenosides at various concentrations, and FIG. 7B shows the graph illustrating the comparison results of the percentage of migrated cells. As can be seen in FIG. 7, it was confirmed that all of the 3 kinds of ginsenosides promoted the migration of HUVECs.

FIG. 8A shows the images illustrating the results of performing cell migration assay of HRMECs cultured by treating with 3 kinds of ginsenosides at various concentrations, and FIG. 8B shows the graph illustrating the comparison results of the percentage of migrated cells. As can be seen in FIG. 8, it was confirmed that all of the 3 kinds of ginsenosides promoted the migration of HRMECs.

Example 5: Vascular Leak-Inhibiting Effect of Ginsenosides

Example 5-1: Analysis of the Effect of Ginsenoside F1 or Rh1 on Vascular Leak at Cellular Level The HUVECs, cultured by a method described in Example 1, were pretreated with 25 μM ginsenoside F1 or Rh1 for 1 hour selected from Example 1, treated with VEGF-A, and then subjected to a vascular permeability assay (FIG. 9). In particular, the cells cultured after treating with DMSO instead of ginsenoside were used as a negative control; the cells cultured after treating with VEGF-A, which is known to promote angiogenesis, were used as a positive control; and the cells pretreated with ginsenoside F1 or Rh1 and not treated with VEGF-A were used as a comparative group.

FIG. 9 shows the graph illustrating the comparison results with regard to the effect of the pretreatment with ginsenoside F1 or Rh1 on vascular leakage induced by treating HUVECs with VEGF-A. As can be seen in FIG. 9, although a high level of vascular leakage occurred when HUVECs were treated with VEGF-A, it was confirmed that the vascular leakage was inhibited by the pretreatment with ginsenoside F1 or Rh1. Furthermore, it was confirmed that the level of vascular leakage when the HUVECs were treated with VEGF-A after the pretreatment with ginsenoside F1 or Rh1 was further reduced compared to when the HUVECs were treated with ginsenoside F1 or Rh1 alone.

Example 5-2: Analysis of In Vivo Effect of Ginsenoside F1 or Rh1 on Vascular Leak Seven-week-old male ICR mice were injected with 1% Evans blue dye (200 μL) into the tail vein and allowed to react for 10 minutes to dye the blood in blue.

Then, the mice were intradermally injected in an amount of 10 μL through the ears with PBS (negative control), VEGF-A (250 μg, positive control), ginsenoside F1 (1.25 μM), ginsenoside Rh1 (1.25 μM), VEGF-A (250 μg)/ginsenoside F1 (1.25 μM), or VEGF-A (250 μg)/ginsenoside Rh1 (1.25 μM), respectively.

Thirty minutes thereafter, the mice were subjected to euthanasia and their ears were removed. After confirming the amount of blood leakage by the naked eye (FIG. 10A), the ears were put in formamide and fixed at 37° C. for 24 hours. Then, the effects of F1 or Rh1 on the inhibition of blood leakage were quantitatively evaluated by measuring the absorbance at 620 nm (FIG. 10B).

FIG. 10A shows the images illustrating the effects of ginsenosides F1 or Rh1 on vascular leak syndrome induced by VEGF-A in mouse ears, confirmed by the naked eye by Evans blue staining, and FIG. 10B shows the graph illustrating the effects of ginsenosides F1 or Rh1 on vascular leak syndrome induced by VEGF-A in mouse ears, confirmed by a quantitative analysis at the level of Evans blue staining.

As can be seen in FIGS. 10A and 10B, it was confirmed that ginsenosides F1 or Rh1 effectively inhibit the vascular leakage symptoms induced by VEGF-A in an in vivo environment as in mice.

From the above, accordingly, it was confirmed that ginsenosides F1 or Rh1 can promote angiogenesis both at a cellular level and at an animal level and also exhibit an effect of suppressing vascular leak.

The invention claimed is:

1. A method for treating vascular leakage syndrome comprising administering a composition comprising ginsenoside F1, ginsenoside Rh1, or a combination thereof to a subject having vascular leakage syndrome.

2. The method of claim 1, wherein the composition further comprises a pharmaceutically acceptable carrier, excipient, or diluent.

\* \* \* \* \*